US006645222B1

(12) United States Patent
Parodi et al.

(10) Patent No.: US 6,645,222 B1
(45) Date of Patent: Nov. 11, 2003

(54) PUNCTURE RESISTANT BRANCH ARTERY OCCLUSION DEVICE AND METHODS OF USE

(75) Inventors: Juan Carlos Parodi, Buenos Aires (AG); Michael J. Horzewski, San Jose, CA (US)

(73) Assignee: Arteria Medical Science, Inc., San Francisco, CA (US)

( * ) Notice: Subject to any disclaimer, the term of this patent is extended or adjusted under 35 U.S.C. 154(b) by 0 days.

(21) Appl. No.: 09/691,295

(22) Filed: Oct. 17, 2000

Related U.S. Application Data

(63) Continuation-in-part of application No. 09/528,958, filed on Mar. 20, 2000, now Pat. No. 6,582,396, which is a continuation-in-part of application No. 09/333,074, filed on Jun. 14, 1999, now Pat. No. 6,206,868, which is a continuation-in-part of application No. PCT/US99/05469, filed on Mar. 12, 1999, which is a continuation-in-part of application No. 09/078,263, filed on Mar. 5, 1998, now Pat. No. 6,413,235.

(51) Int. Cl.[7] ............................................. A61M 29/00
(52) U.S. Cl. ................. 606/200; 604/96.01; 604/103.05
(58) Field of Search ..................... 604/96.01, 103.05, 604/98.01, 99.01, 102.02, 171, 194, 97.01, 103.1; 606/200

(56) References Cited

U.S. PATENT DOCUMENTS

| | | | |
|---|---|---|---|
| 4,794,928 A | 1/1989 | Kletschka | |
| 4,921,478 A | 5/1990 | Solano et al. | |
| 5,011,488 A | 4/1991 | Ginsburg | |
| 5,102,415 A | 4/1992 | Guenther et al. | |
| 5,549,626 A | 8/1996 | Miller et al. | |
| 5,584,803 A | 12/1996 | Stevens et al. | |
| 5,669,927 A | 9/1997 | Boebel et al. | |
| 5,766,151 A | 6/1998 | Valley et al. | |
| 5,766,203 A | * 6/1998 | Imran et al. | 604/96.01 |
| 5,833,650 A | 11/1998 | Imran | |
| 5,843,027 A | * 12/1998 | Stone et al. | 604/103.05 |
| 5,895,399 A | 4/1999 | Barbut et al. | |
| 5,916,193 A | 6/1999 | Stevens et al. | |
| 5,925,016 A | 7/1999 | Chornenky et al. | |
| 5,997,557 A | 12/1999 | Barbut et al. | |
| 6,013,085 A | 1/2000 | Howard | |
| 6,027,476 A | 2/2000 | Sterman et al. | |
| 6,029,671 A | 2/2000 | Stevens et al. | |
| 6,042,559 A | 3/2000 | Dobak, III | |
| 6,099,497 A | * 8/2000 | Adams et al. | 604/101.01 |
| 6,120,477 A | * 9/2000 | Campbell et al. | 604/96.01 |
| 6,129,708 A | 10/2000 | Enger | |
| 6,180,059 B1 | 1/2001 | Divino, Jr. et al. | |
| 6,228,052 B1 | 5/2001 | Pohndorf | |
| 6,295,989 B1 | 10/2001 | Connors, III | |

FOREIGN PATENT DOCUMENTS

EP 0 427 429 A2 5/1991

* cited by examiner

*Primary Examiner*—Brian L. Casler
*Assistant Examiner*—Kevin C. Sirmons
(74) *Attorney, Agent, or Firm*—Luce, Forward, Hamilton & Scripps; Nicola A. Pisano

(57) ABSTRACT

Methods and apparatus are provided for removing emboli during an angioplasty, stenting, or surgical procedure comprising apparatus for occluding a branch artery to prevent reversal of flow during carotid artery stenting, the apparatus comprising a retrieval sheath configured to reduce the risk of potentially dangerous interaction with the stent during retrieval.

17 Claims, 6 Drawing Sheets

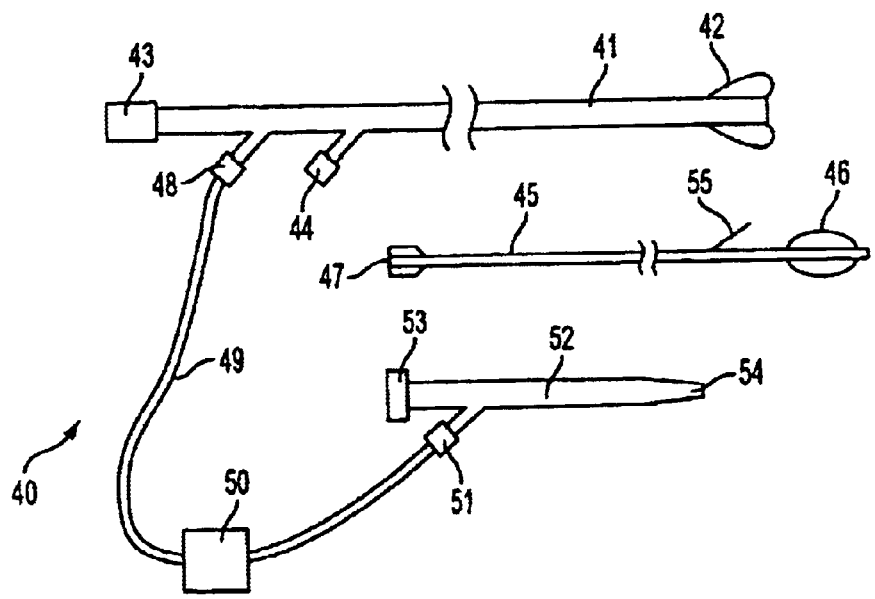
FIG. 2A
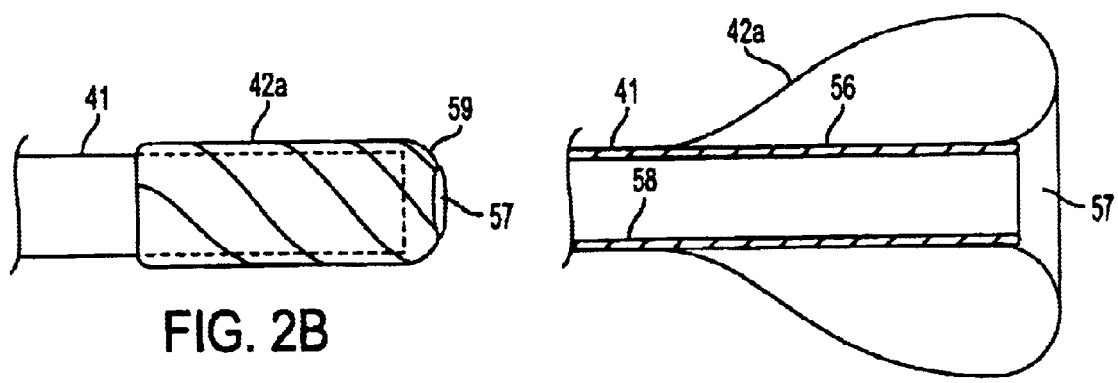
FIG. 2B
FIG. 2C
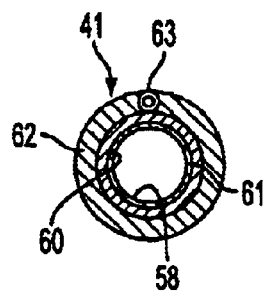
FIG. 2D

PUNCTURE RESISTANT BRANCH ARTERY OCCLUSION DEVICE AND METHODS OF USE

REFERENCE TO RELATED APPLICATIONS

The present application is a continuation-in-part of U.S. patent application Ser. No. 09/528,958, filed Mar. 20, 2000, now U.S. Pat. No. 6,582,396 which is a continuation-in-part of U.S. patent application Ser. No. 09/333,074, filed Jun. 14, 1999 now U.S. Pat. No. 6,206,868, which is a continuation-in-part of International Application PCT/US99/05469, filed Mar. 12, 1999, which is a continuation-in-part of U.S. patent application Ser. No. 09/078,263, filed Mar. 5, 1998, now U.S. Pat. No. 6,413,235.

FIELD OF THE INVENTION

This invention relates to apparatus and methods for occluding a body lumen. More particularly, the present invention provides a puncture resistant occlusion balloon, suitable for use, for example, during transluminal stenting of the carotid arteries.

BACKGROUND OF THE INVENTION

Carotid artery stenoses typically manifest in the common carotid artery, internal carotid artery or external carotid artery as a pathologic narrowing of the vascular wall, for example, caused by the deposition of plaque, that inhibits normal blood flow. Endarterectomy, an open surgical procedure, traditionally has been used to treat such stenosis of the carotid artery.

In view of the trauma and long recuperation times generally associated with open surgical procedures, considerable interest has arisen in the endovascular treatment of carotid artery stenosis. In particular, widespread interest has arisen in transforming interventional techniques developed for treating coronary artery disease, such as stenting, for use in the carotid arteries. Such endovascular treatments, however, are especially prone to the formation of emboli.

Such emboli may be created, for example, when an interventional instrument, such as a guide wire or angioplasty balloon, is forcefully passed into or through the stenosis, as well as after dilatation and deflation of the angioplasty or stent deployment balloon. Because such instruments are advanced into the carotid artery in the same direction as blood flow, emboli generated by the procedure are carried directly into the brain by antegrade blood flow.

Stroke rates after carotid artery stenting have varied widely in different clinical series, from as low as 4.4% to as high as 30%. One review of carotid artery stenting including data from twenty-four major interventional centers in Europe, North America, South America, and Asia had a combined initial failure and combined mortality/stroke rate of more than 7%. Cognitive studies and reports of intellectual changes after carotid artery stenting indicate that embolization is a common event causing subclinical cerebral damage.

Several previously known apparatus and methods attempt to remove emboli formed during endovascular procedures by occluding blood flow and trapping or suctioning the emboli out of the vessel of interest. These previously known systems, however, provide less than optimal solutions to the problems of effectively removing emboli generated during stenting. The elements used to occlude blood flow may, for example, dangerously interact with a stent.

Chapter 46 of *Interventional Neuroradiology: Strategies and Practical Techniques* (J. J. Connors & J. Wojak, 1999), published by Saunders of Philadelphia, Pa., describes use of a coaxial balloon angioplasty system for patients having proximal internal carotid artery ("ICA") stenoses. In particular, a small, deflated occlusion balloon on a wire is introduced into the origin of the external carotid artery ("ECA"), and a guide catheter with a deflated occlusion balloon is positioned in the common carotid artery ("CCA") just proximal to the origin of the ECA. A dilation catheter is advanced through a lumen of the guide catheter and dilated to disrupt the stenosis. Before deflation of the dilation catheter, the occlusion balloons on the guide catheter and in the ECA are inflated to block antegrade blood flow to the brain. The dilation balloon then is deflated, the dilation catheter is removed, and blood is aspirated from the ICA to remove emboli.

EP Publication No. 0 427 429 describes a similar device with a first balloon for occluding a patient's CCA, and a second balloon for occluding the patient's ECA prior to crossing a lesion in the ICA.

A drawback of both the device in EP Publication No. 0 427 429 and the *Interventional Neuroradiology* device is that, if either is used to place a stent in the ICA, the stent may extend beyond the bifurcation between the ECA and the ICA. The occlusion balloon placed by guide wire in the ECA may then snag the stent during retrieval, causing the balloon to puncture or get caught within the artery, and requiring emergency surgery to remove the balloon.

In view of drawbacks associated with previously known systems, it would be desirable to provide methods and apparatus for removing emboli from within the carotid arteries during carotid stenting that simultaneously reduce the risk of emboli being carried into the cerebral vasculature while preventing dangerous interaction between the apparatus and the stent.

SUMMARY OF THE INVENTION

In view of the foregoing, it is an object of the present invention to provide methods and apparatus for removing emboli from within branched arteries during stenting that simultaneously reduce the risk of emboli being carried into the patient's vasculature, e.g., cerebral vasculature, while preventing dangerous interaction between the apparatus and the stent.

The foregoing objects of the present invention are accomplished by providing interventional apparatus for occluding flow in a branch artery, the apparatus being resistant to puncture. The apparatus preferably is employed in conjunction with an arterial catheter, a venous return catheter, and, optionally, a blood filter or flow control valve disposed between the arterial and venous return catheters. The arterial catheter has proximal and distal ends, an aspiration lumen extending therebetween, an occlusion element disposed on the distal end, and a hemostatic port and blood outlet port disposed on the proximal end that communicate with the aspiration lumen. The aspiration lumen is sized so that an interventional instrument, e.g., a stent delivery system, may be readily advanced therethrough to the site of a stenosis in either the ECA (proximal to the balloon) or the ICA.

The arterial catheter illustratively is disposed in the CCA proximal of the ICA/ECA bifurcation, the branch artery occlusion device is disposed in the ECA to occlude flow reversal from the ECA to the ICA, and the blood outlet port of the arterial catheter is coupled to the venous return catheter, with or without the blood filter disposed therebetween. Higher arterial than venous pressure, especially during diastole, permits low-rate flow reversal in the ICA during an interventional procedure (other than when a dilatation balloon is inflated) to flush blood containing emboli from the vessel. The blood may be filtered and reperfused into the body through the venous return catheter.

In accordance with the principles of the present invention, the branch artery occlusion device is puncture resistant, so as to prevent dangerous interaction between the balloon and a stent during retrieval. In a first embodiment, the device includes a wedge configured to deflect the balloon away from contacting a portion of the stent extending past the ECA/ICA bifurcation during balloon retrieval. In a second embodiment, the device comprises a balloon that retracts into a capsule prior to retrieval of the balloon from the ECA. In a third embodiment, a sheath is advanced over the balloon prior to retrieval from the ECA.

Methods of using the apparatus of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIGS. 2A–2D are, respectively, a schematic view, and detailed side and sectional views of the distal end of a system employing a branch artery occlusion device of the present invention;

DESCRIPTION OF THE PREFERRED EMBODIMENTS

Figure 1A:
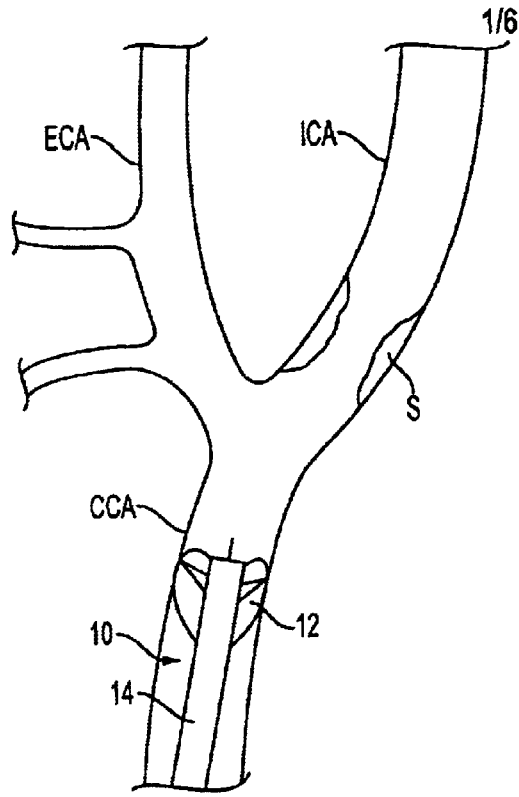
FIGS. 1A–1C are schematic views depicting a prior art method of emboli protection during carotid stenting.
Figure 1B:
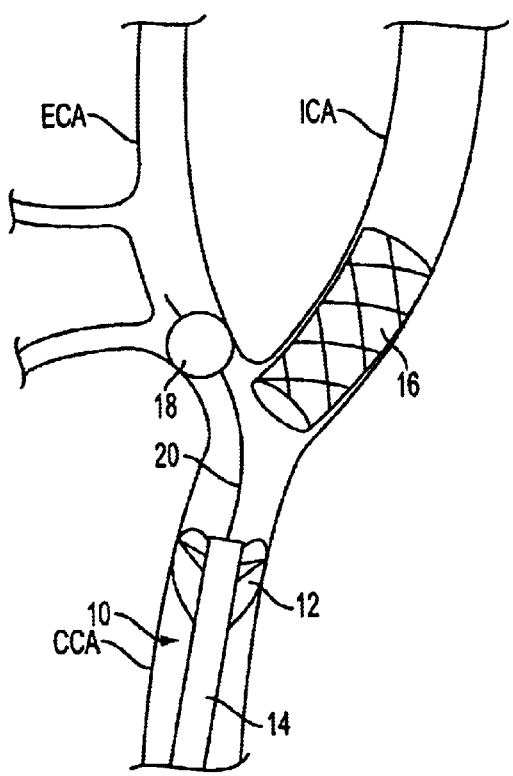
Figure 1C:
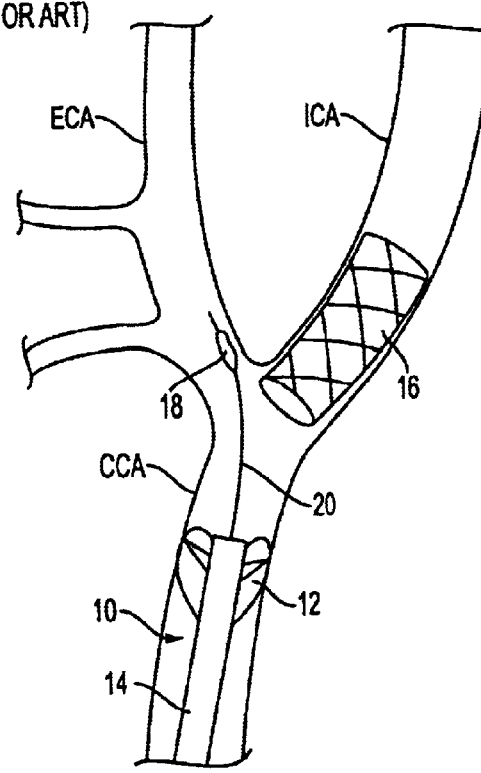

Referring to FIGS. 1A–1C, drawbacks of previously known emboli removal catheters are described with reference to performing carotid stenting in internal carotid artery ICA. Naturally-aspirated or vacuum suction emboli removal system 10, such as described in the above-mentioned *Interventional Neuroradiology* article and in the European Patent Publication, is disposed in common carotid artery CCA. As seen in FIG. 1A, inflation member 12, disposed on the distal end of emboli removal catheter 14, is inflated to occlude flow in the CCA.

Applicant has determined that once member 12 is inflated, flow within the external carotid artery ECA reverses and provides antegrade flow into the ICA, due to the lower hemodynamic resistance of the ICA. Consequently, emboli generated while passing stent 16 across stenosis S may be carried irretrievably into the cerebral vasculature—before flow in the vessel is reversed and directed into the aspiration lumen of emboli removal catheter 14 by opening the proximal end of the aspiration lumen to atmospheric pressure or suction.

To solve this problem, previously known methods teach the use of an occlusion balloon to stop the development of retrograde flow from the ECA to the ICA. Thus, as depicted in FIG. 1B, balloon 18 on wire 20 is advanced into and occludes the ECA prior to placement of stent 16 in the ICA. Once stent 16 is in place, balloon 18 is deflated, and wire 20 is retracted, as depicted in FIG. 1C. System 10 then may be removed from the patient. However, when stent 16 extends beyond the ECA/ICA bifurcation, a common problem experienced in clinical practice is snagging of balloon 18 on stent 16 during retrieval of balloon 18. Balloon 18 may puncture or may occlude the ECA, requiring emergency open surgery to remove the balloon and reopen the vessel.

The present invention is directed to an improved branch artery occlusion device for use in occluding the ECA. Specifically, in accordance with the principles of the present invention, the occlusion balloon is puncture resistant and is designed to reduce snagging or puncture during retrieval.

Referring now to FIG. 2A, embolic protection apparatus 40, suitable for use with the branch artery occlusion device 45 of the present invention, is described. Apparatus 40 comprises arterial catheter 41, venous return line 52, tubing 49, and optional blood filter or flow control valve 50. Catheter 41 includes distal occlusion element 42, proximal hemostatic port 43, (e.g., a Touhy-Borst connector) inflation port 44, and blood outlet port 48. Tubing 49 couples blood outlet port 48 to filter 50 and blood inlet port 51 of venous return line 52.

More specifically, with respect to FIGS. 2B and 2C, distal occlusion element 42 comprises expandable bell or pear-shaped balloon 42a. In accordance with manufacturing techniques that are known in the art, balloon 42a comprises a compliant material, such as polyurethane, latex, or polyisoprene, which has variable thickness along its length to provide a bell-shape when inflated. Balloon 42a is affixed to distal end 56 of catheter 41, for example, by gluing or a melt-bond, so that opening 57 in balloon 42a leads into aspiration lumen 58 of catheter 41. Balloon 42a preferably is wrapped and heat treated during manufacture so that distal portion 59 extends beyond the distal end of catheter 41 and provides an atraumatic tip or bumper for the catheter.

As shown in FIG. 2D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 42a. In a preferred embodiment of catheter 41, the diameter of lumen 58 is approximately 7 Fr, and the outer diameter of the catheter is approximately 9 Fr.

Venous return line 52 includes hemostatic port 53, blood inlet port 51 and a lumen that communicates with ports 53 and 51 and tip 54. Venous return line 52 may be constructed in a manner per se known for venous introducer catheters. Tubing 49 may comprise a suitable length of a biocompatible material, such as silicone. Alternatively, tubing 49 may be omitted, and blood outlet port 48 of catheter 41 and blood inlet port 51 of venous return line 52 may be lengthened to engage either end of filter 50 or each other.

Still referring to FIG. 2A, embolic protection apparatus 40 further comprises branch artery occlusion device 45 of the present invention having balloon 46 that is inflated via inflation port 47. Device 45, including balloon 46, is configured to pass through hemostatic port 43 and the aspiration lumen of catheter 41 (see FIGS. 2C and 2D), so that the balloon may be advanced into and occlude the ECA. Port 43 and the aspiration lumen of catheter 41 are sized to permit additional interventional devices, such as angioplasty balloon catheters, atherectomy devices and stent delivery systems to be advanced through the aspiration lumen when device 45 is deployed.

In accordance with a first embodiment of the present invention, device 45 comprises means for reducing puncture of balloon 46, illustratively wedge 55. Wedge 55 preferably comprises a resilient material, such as a polymer or resilient wire, and reduces the risk that balloon 46 will puncture or snag on a portion of a stent that extends beyond the bifurcation of the ICA and ECA. Preferably, device 45 further comprises a small diameter elongated tubular member having an inflation lumen that couples inflatable balloon 46 to inflation port 47. Inflatable balloon 46 preferably comprises a compliant material, such as described hereinabove with respect to occlusion element 42 of emboli removal catheter 41.

Referring now to FIGS. 3A–3D, use of the apparatus of FIG. 2 in accordance with the methods of the present invention during carotid stenting is described. First, a flow of blood is induced between the treatment site (e.g., carotid artery) and the patient's venous vasculature (e.g., femoral vein). Because blood flow through the artery is towards catheter 41, any emboli dislodged by advancing a stent across stenosis S causes the emboli to be aspirated by catheter 41.

Figure 3A:
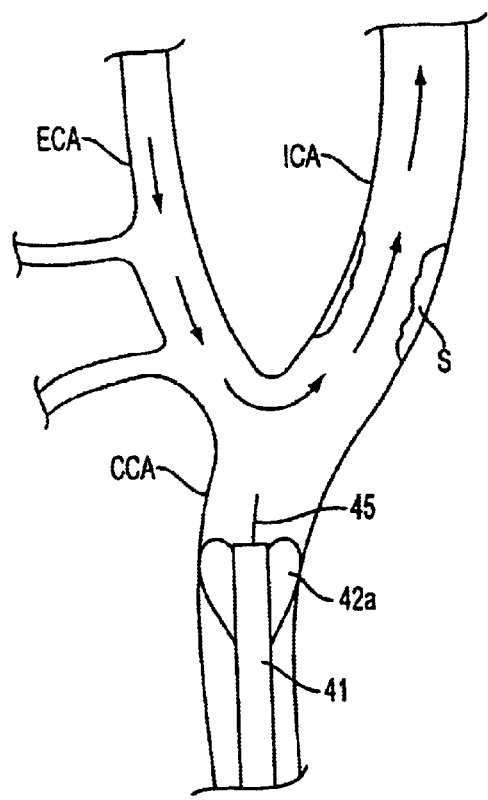
FIGS. 3A–3D illustrate a method of using the apparatus of FIG. 2 in accordance with the principles of the present invention.

In FIG. 3A, stenosis S is located in internal carotid artery ICA above the bifurcation between the internal carotid artery ICA and the external carotid artery ECA. Catheter 41 is inserted, either percutaneously and transluminally or via a surgical cut-down, to a position proximal of stenosis S, without causing the distal end of device 45 to cross the stenosis. Balloon 42a of distal occlusion element 42 is then inflated, preferably with a radiopaque contrast solution, via inflation port 44. This creates reversal of flow from the external carotid artery ECA into the internal carotid artery ICA.

Figure 3B:
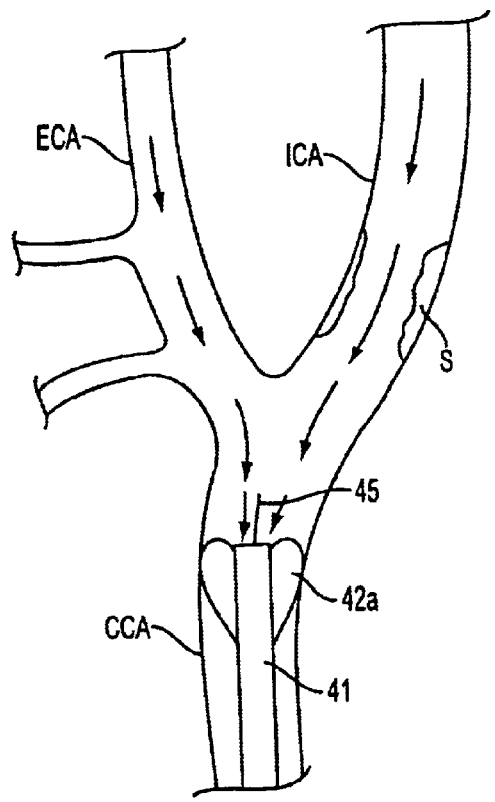

Venous return line 52 then is introduced into the patient's femoral vein, either percutaneously or via a surgical cut-down. Filter 50 is coupled between blood outlet port 48 of catheter 41 and blood inlet port 51 of venous return line 52 using tubing 49, and any air is removed from the line. Once this circuit is closed, negative pressure in the venous catheter during diastole establishes a low rate flow of blood through aspiration lumen 58 of catheter 41, as seen in FIG. 3B, to the patient's vein via venous return line 52.

This low rate flow, due to the difference between venous pressure and arterial pressure, preferably continues throughout the interventional procedure. Specifically, blood passes through aspiration lumen 58 and blood outlet port 48 of catheter 41, through biocompatible tubing 49 to filter 50, and into blood inlet port 51 of venous return line 52, where it is reperfused into the remote vein. Filtered emboli collect in filter 50 and may be studied and characterized upon completion of the procedure.

Figure 3C:
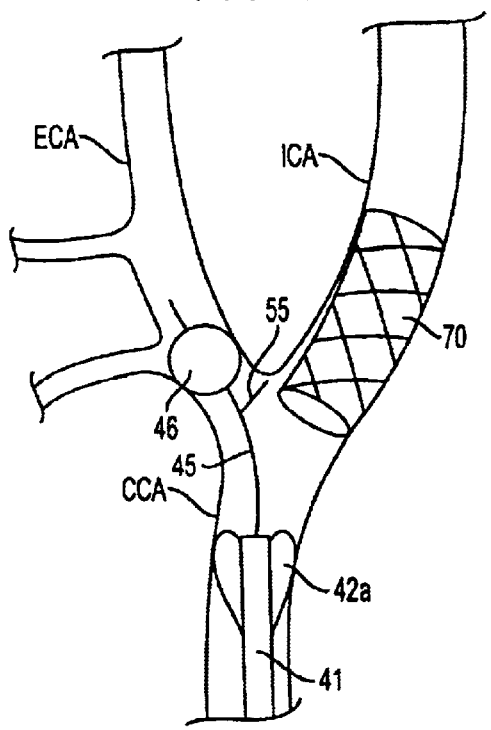

Referring to FIG. 3C, with balloon 42a of occlusion element 42 inflated and a retrograde flow established in the ICA, device 45 is advanced through aspiration lumen 58.

When balloon 46 is disposed within the ECA, as determined, e.g., using a fluoroscope and a radiopaque inflation medium injected into balloon 46, balloon 46 is inflated. Occlusion of the ECA prevents the development of reverse flow in the ECA from causing antegrade flow in the ICA. Another interventional instrument, such as stent 70, may be loaded through hemostatic port 43 and aspiration lumen 58 and positioned across stenosis S to ensure proper blood flow to the ICA.

It is often desirable for stent 70 to extend beyond the bifurcation between the ECA and the ICA. Consequently, when the occlusion balloon of device 45 is deflated and withdrawn from the ECA, there is a risk that the balloon may snag on the stent. In such cases, emergency surgery may be required to remove the balloon.

Figure 3D:
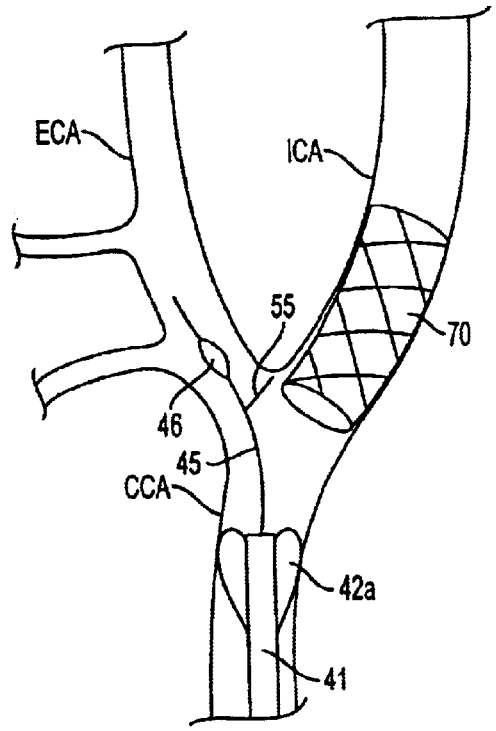

As shown in FIG. 3D, upon completion of the stenting portion of the procedure, balloon 46 is deflated, and device 45 is prepared for retraction. Because balloon 46 is disposed on a small diameter elongated tubular member, rather than a traditional, larger diameter balloon catheter, its cross-sectional diameter is significantly reduced, and thus the risk that the balloon will snag or puncture on stent 70 is reduced. Resilient wedge 55 further reduces risk by urging the balloon outward away from the stent during retrieval of device 45. Device 45, emboli removal catheter 41, and venous return line 52 are then removed from the patient, completing the procedure.

Optionally, increased volumetric blood flow through the extracorporeal circuit may by achieved by attaching an external pump, such as a roller pump (not shown), to tubing 49. If deemed beneficial, the external pump may be used in conjunction with apparatus 40 at any point during the interventional procedure.

Throughout the procedure, except when the dilatation balloon is fully inflated, the pressure differential between the blood in the ICA and the venous pressure causes blood in the ICA to flow in a retrograde direction into aspiration lumen 58 of emboli removal catheter 41, thereby flushing any emboli from the vessel. The blood is filtered and reperfused into the patient's vein.

As set forth above, the method of the present invention protects against embolization, first, by preventing the reversal of blood flow from the ECA to the ICA when distal occlusion element 42 is inflated and hemostatic port 43 is open, and second, by providing continuous, low volume blood flow from the carotid artery to a remote vein in order to filter and flush any emboli from the vessel and blood stream. Advantageously, the method of the present invention permits emboli to be removed with little blood loss, because the blood is filtered and reperfused into the patient. Furthermore, continuous removal of blood containing emboli prevents emboli from migrating too far downstream for aspiration.

Figure 4A:
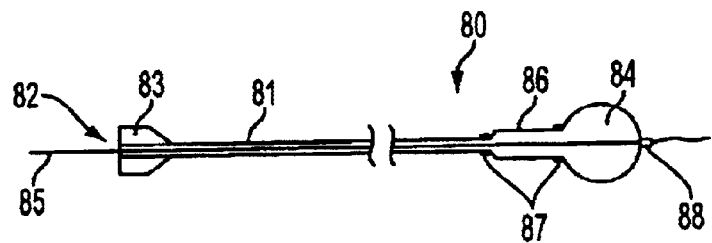
FIGS. 4A and 4B are schematic views of an alternative embodiment of the branch artery occlusion device of the apparatus of FIG. 2, shown, respectively, in a deployed configuration and in a retrieval configuration.
Figure 4B:
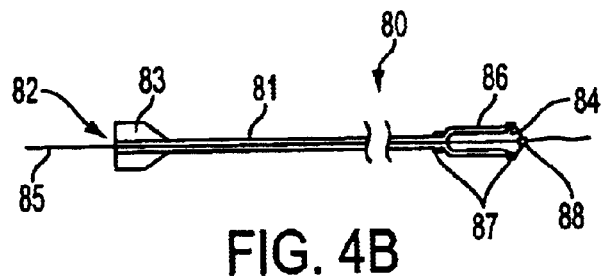

Referring now to FIGS. 4A and 4B, an alternative embodiment of the branch artery occlusion device of the present invention is described. Occlusion device 80 comprises small diameter elongated tubular member 81 having inflation lumen 82 and proximally terminating in inflation port 83, occlusion balloon 84, core wire 85 attached to balloon 84, capsule 86, radiopaque capsule features 87, and radiopaque balloon feature 88. Core wire 85 is preferably approximately 0.010" in diameter and is configured to be received within inflation lumen 82 of tubular member 81. Tubular member 81 preferably is approximately 0.018" in diameter.

Balloon 84 may be inflated via inflation lumen 82 with a standard or radiopaque inflation medium. Balloon 84 then extends distally of, but remains attached to, capsule 86. Upon completion of an interventional procedure, such as carotid stenting, balloon 84 is deflated. Proximal retraction of core wire 85 draws balloon 84 into capsule 86, thereby preventing snagging during retrieval.

Figure 5A:
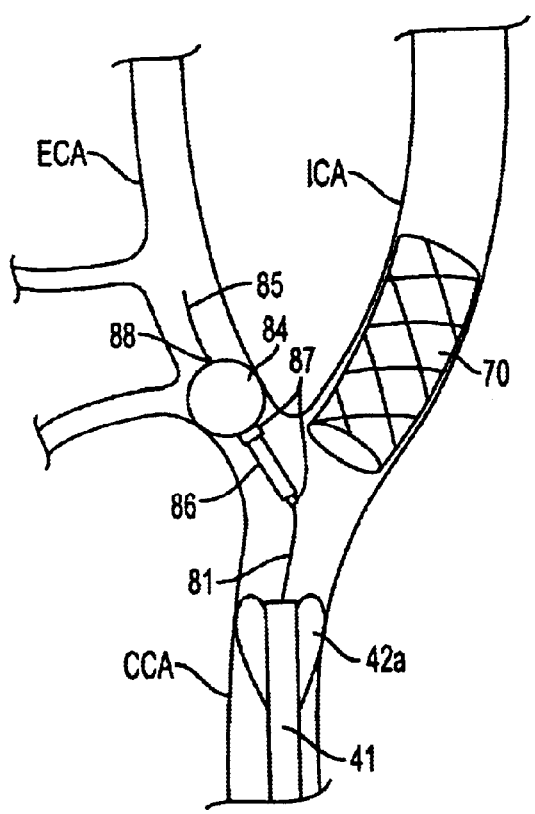
FIGS. 5A–5B illustrate a method of using the apparatus of FIG. 4 in accordance with the principles of the present invention.
Figure 5B:
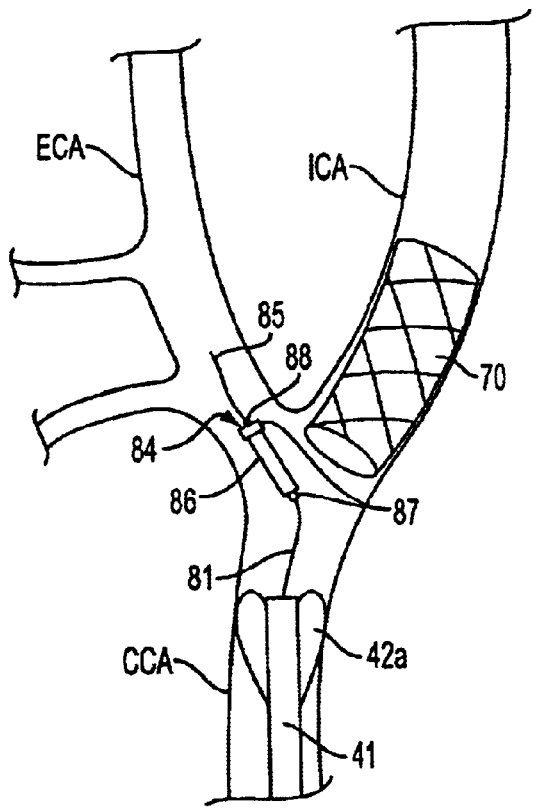

Referring now to FIGS. 5A and 5B, use of occlusion apparatus 80 in conjunction with arterial catheter 41 and venous return catheter 52 of FIG. 2 during carotid stenting is described. With balloon 42a of occlusion element 42 inflated and a retrograde flow established in the ICA as described hereinabove, occlusion apparatus 80 is advanced through aspiration lumen 58 of catheter 41. Capsule 86 is disposed just within the ECA, as determined, e.g., using a fluoroscope and radiopaque capsule features 87, as seen in FIG. 5A. Occlusion balloon 84 is then inflated and its position verified by, for example, a fluoroscope and radiopaque balloon feature 88 or a radiopaque inflation medium injected into balloon 84. Occlusion of the ECA prevents the development of reverse flow in the ECA from causing antegrade flow in the ICA. Another interventional instrument, such as stent 70, is then loaded through hemostatic port 43 and aspiration lumen 58 and positioned across stenosis S to ensure proper blood flow to the ICA.

As discussed hereinabove, it is often desirable for stent 70 to extend beyond the bifurcation between the ECA and the ICA. Consequently, when the balloon of the branch artery occlusion device is deflated and withdrawn from the ECA, there is a risk that the balloon may snag on the stent, with potentially dire consequences.

As shown in FIG. 5B, upon completion of the stenting portion of the procedure, balloon 84 is deflated, and core wire 85 is proximally retracted to draw deflated balloon 84 within capsule 86. Because balloon 84 is disposed on small diameter tubular member 81 instead of a traditional, larger diameter balloon catheter, its cross-sectional diameter is significantly reduced, and thus the risk that the balloon will snag or puncture on stent 70 is reduced. Capsule 86 further reduces this risk by protecting the balloon during retrieval of occlusion apparatus 80. Apparatus 80, emboli removal catheter 41, and venous return line 52 then are removed from the patient, completing the procedure.

Figure 6A:
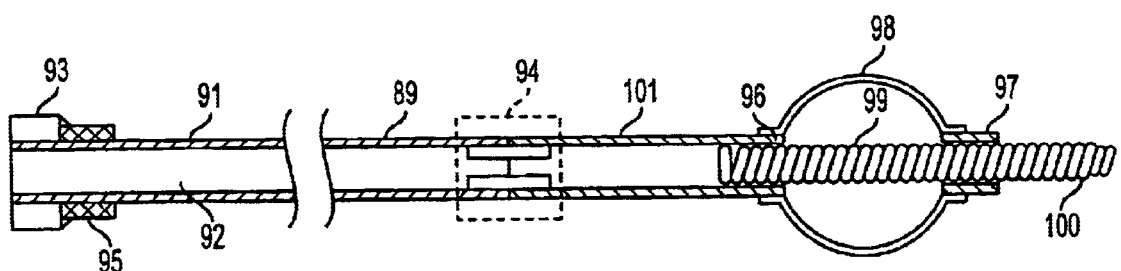
FIG. 6A is a sectional view of an alternative embodiment of the branch artery occlusion device suitable for use in conjunction with the apparatus of FIG. 2.
Figure 6B:
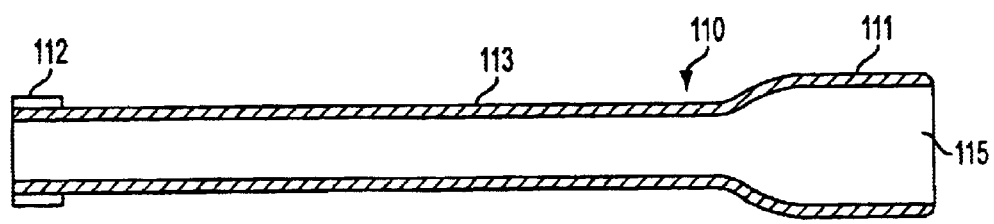
FIG. 6B is a sectional view of a retrieval sheath for use with the occlusion device of FIG. 6A.

Referring now to FIGS. 6A and 6B, another alternative embodiment of the branch artery occlusion device of the present invention is described. Occlusion device 90 comprises small diameter elongated tubular member 89 having proximal portion 91 and distal portion 101 that are joined at junction 94, inflation lumen 92 which spans the length of member 89 and terminates in inflation port 93, strain relief 95, occlusion balloon 98, and coil 99. Coil 99 extends through occlusion balloon 98 to form a floppy-tip guide wire 100.

As shown in FIG. 6A, proximal and distal portions 91 and 101 preferably have substantially equal internal and external diameters, so as to form a substantially continuous tubular member 89 when joined together at junction 94. Proximal portion 91 preferably is constructed using materials known for use in catheter construction, such as a polytetrafluoroethylene ("PTFE")-coated stainless steel hypotube. Distal portion 101 preferably is constructed using a flexible material, such as polyamide. Distal portion 101 may include particles of a radioopaque material, e.g., tantalum or platinum, to enhance radioopacity of the distal portion when viewed using a fluoroscope. This in turn improves positioning of the device within the patient's vasculature.

Figure 7A:
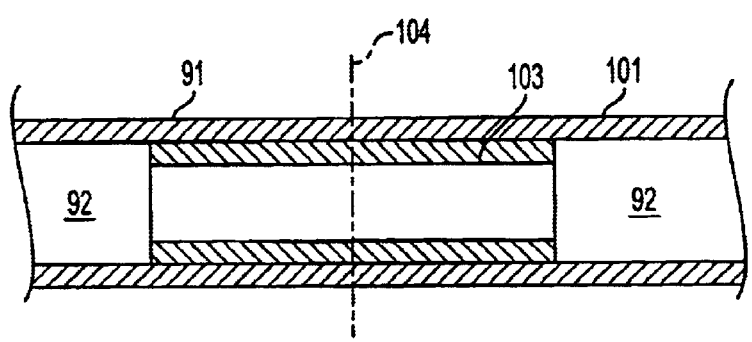
FIGS. 7A and 7B are sectional views of illustrative junctions suitable for use in making the branch artery occlusion device of FIG. 6A.
Figure 7B:
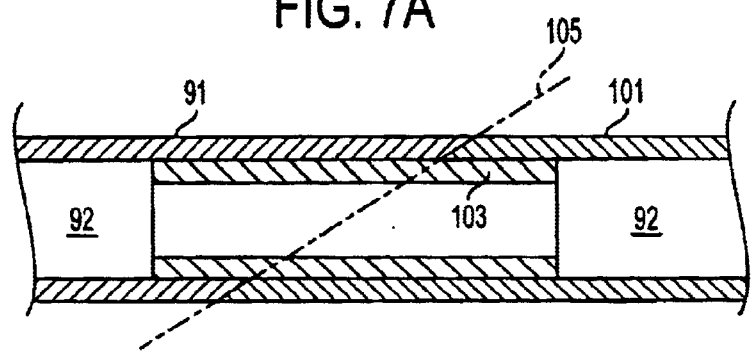

Detailed views of illustrative junctions 94 are described with respect to FIGS. 7A and 7B. In FIG. 7A, proximal portion 91 forms a butt joint with distal portion 101 at substantially a right angle, as indicated by dotted line 104. The distal and proximal portions are connected at junction 94 by tube 103, which is disposed within lumen 92, for example, using an ultra-violet adhesive, shrink welding, or other suitable bonding technique. The resulting bond at junction 94 is strong enough to withstand the rotational forces commonly associated with intervention procedures without suffering from kinking or twisting.

In FIG. 7B, another illustrative embodiment of junction 94 includes proximal portion 91 abutting distal portion 101 at an acute angle, as indicated by dotted line 105. The two portions may be attached together as described above. It will be understood, that these configurations are merely exemplary and that other junction configurations also may be used without departing from the scope of the invention. Junction 94, for example, may include irregular or jagged surfaces that are constructed to interlock together at acute, right, or obtuse angles, etc.

Referring back to FIG. 6A, branch artery occlusion device 90 includes coil 99. Coil 99 preferably is constructed of a resilient material, such as platinum or nitinol, and preferably extends beyond the distal end of short tubular member 97 to form floppy tip 100. Coil 99 is anchored to proximal shoulder 96 of tubular member 101 and permits inflation medium applied via port 93 to communicate with the interior of balloon 98. Coil 99 enhances the rigidity balloon 98, making the balloon less susceptible to twisting an bunching during placement. Floppy tip 100 also facilitates navigation of balloon 98 to a desired treatment area.

The length and/or spring coefficient of coil 99 may be varied depending on the desired degree of rigidity desired for balloon 98. Preferably, coil 99 extends beyond tubular member 97 by about 0.5" and extends proximally of proximal shoulder 96 by about an equal length. Of course, it will be understood that other dimensions also may be used without departing from the scope of the invention. For example, coil 99 may extend outward from tubular member 97 by about 0.75" and extend through balloon 98 all the way to junction 94.

Balloon 98 preferably has a length in a range of 5–15 mm, and is inflated via inflation lumen 92 with a standard or radiopaque inflation medium. Upon completion of an interventional procedure, such as carotid stenting, balloon 98 is deflated. Rather than using the retraction system described above, however, where retraction of a core wire collapses a balloon into a capsule, branch artery occlusion device 90 employs a sheath advancing technique that surrounds balloon 98 to prevent snagging during retrieval.

In FIG. 6B, retraction sheath 110 includes expanded distal end 111 forming cavity 115, proximal end 112, and body portion 113. As will of course be understood, sheath 110 is slidably disposed on elongated tubular member 89 proximally of balloon 98 (e.g., before inflation port 93 and strain relief 95 are assembled). Upon completion of an interventional procedure, such as stent deployment, retraction sheath 110 may be advanced over tubular member 89 in the direction indicated by arrow 114. Expanded distal end 111 surrounds balloon 98 to prevent the balloon from undesirably snagging or catching on material within the patient's artery or vein. Once surrounded, occlusion device 90 and retraction sheath 110 are removed together (in a direction opposite arrow of arrow 114) and the procedure is complete.

Figure 8A:
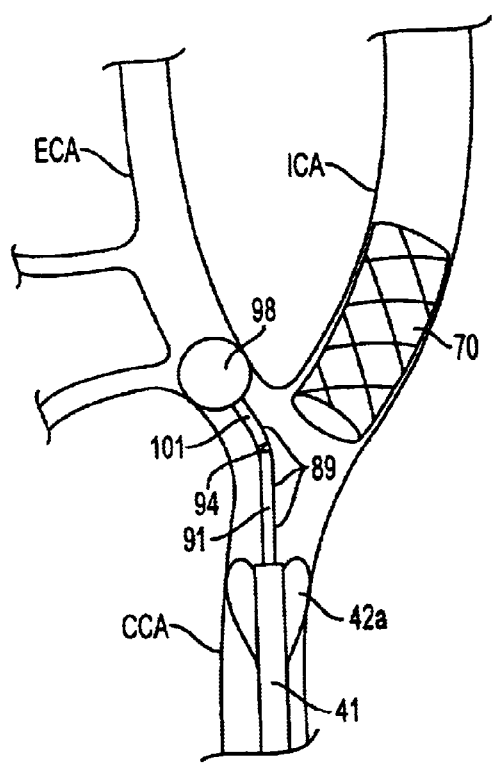
FIGS. 8A–8B illustrate a method of using the apparatus of FIGS. 6A and 6B in accordance with the principles of the present invention.
Figure 8B:
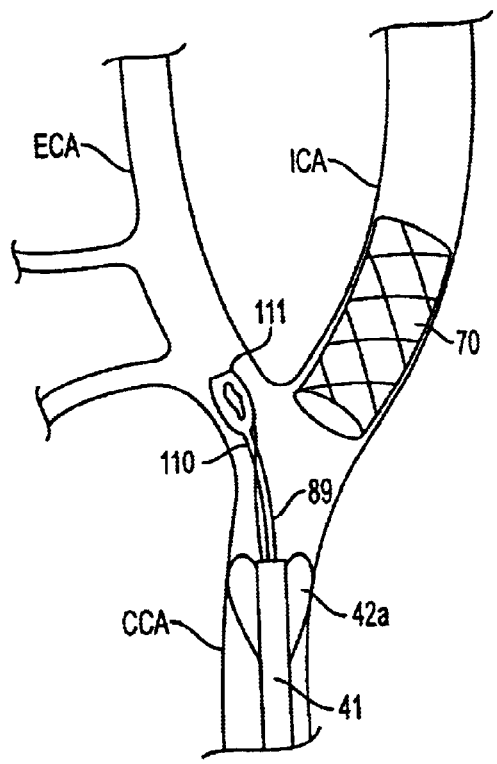

Referring now to FIGS. 8A and 8B, use of occlusion device 90 in conjunction with arterial catheter 41 and venous return catheter 52 of FIG. 2 during carotid stenting is described. With balloon 42a of occlusion element 42 inflated and a retrograde flow established in the ICA as described hereinabove, occlusion apparatus 90 is advanced through aspiration lumen 58 of catheter 41. Balloon 98 is disposed within the ECA, as determined, e.g., using a fluoroscope and radiopaque features of distal portion 101, as seen in FIG. 6A. Occlusion balloon 98 is then inflated and its position verified by, for example, a fluoroscope and a radiopaque inflation medium injected into balloon 98. Occlusion of the ECA prevents the development of reverse flow in the ECA from causing antegrade flow in the ICA. Another interventional instrument, such as stent 70, may then be loaded through hemostatic port 43 and aspiration lumen 58 and positioned across stenosis S to ensure proper blood flow to the ICA.

As discussed hereinabove, it is often desirable for stent 70 to extend beyond the bifurcation between the ECA and the ICA. Consequently, when occlusion balloon 98 on member 89 is deflated and withdrawn from the ECA, there is a risk that the balloon may snag on the stent or other venous material, with potentially dire consequences.

As shown in FIG. 7B, upon completion of the stenting portion of the procedure, balloon 98 is deflated, and retraction sheath 110 is advanced distally along tubular member 89 to surround deflated balloon 98 within expanded distal end 111. Retrieval sheath 110 reduces the risk of snagging the balloon on the stent by protecting the balloon during retrieval of occlusion device 90. Apparatus 90, emboli removal catheter 41, and venous return line 52 then are removed from the patient, completing the procedure.

As will of course be understood, the apparatus of the present invention may be used in locations other than the carotid arteries. They may, for example, be used in the coronary arteries, or in any other location deemed useful.

While preferred illustrative embodiments of the invention are described above, it will be apparent to one skilled in the art that various changes and modifications may be made. The appended claims are intended to cover all such changes and modifications that fall within the true spirit and scope of the invention.

What is claimed is:

1. Apparatus for removing emboli during an angioplasty or stenting procedure, the apparatus comprising:
   an elongated tubular member having proximal and distal ends and a lumen extending therebetween, wherein the elongated tubular member comprises discrete proximal and distal sections connected at a junction;
   an inflation port coupled to the proximal end of the tubular member in communication with the lumen;
   a short tubular member;
   an inflatable member having a proximal end coupled to the distal section and a distal end coupled to the short tubular member, the inflatable member in communication with the lumen;
   a coil having a proximal end coupled to the distal end of the elongated tubular member and the short tubular member, the coil having a length that extends through the inflatable member and the short tubular member to form a floppy tip; and
   a sheath slidably disposed on the tubular member, the sheath including a radially enlarged distal end adapted to selectably enclose the inflatable member during retrieval.

2. The apparatus of claim 1 further comprising a tube fixedly disposed within the lumen to support the junction.

3. The apparatus of claim 1 wherein at least a portion of the distal section is radiopaque.

4. The apparatus of claim 1 wherein at inflatable member has a deployed state and retrieval state.

5. The apparatus of claim 1 further comprising:
   a catheter having proximal and distal ends, a lumen extending therethrough, and a blood outlet port in communication with the lumen, the catheter adapted to be disposed in a patient's carotid artery, the elongated tubular member and inflatable member configured to pass through the lumen;
   an occlusion element disposed on the distal end of the catheter and having an opening that communicates with the lumen, the occlusion element having a contracted state suitable for transluminal insertion and an expanded state wherein the occlusion element occludes antegrade flow in the artery;
   a venous return catheter having proximal and distal ends, a lumen extending therethrough, and a blood inlet port in communication with the lumen; and
   tubing that couples the blood outlet port to the blood inlet port.

6. The apparatus of claim 5 further comprising a blood filter coupled between the blood outlet port and the blood inlet port.

7. The apparatus of claim 5 wherein the occlusion element is a balloon.

8. The apparatus of claim 5 further comprising a pump that removes blood through the catheter and reperfuses blood via the venous return catheter.

9. Apparatus for removing emboli during an angioplasty or stenting procedure, the apparatus comprising:
   an elongated tubular member having proximal and distal ends and a lumen extending therebetween;
   an inflation port coupled to the proximal end of the tubular member in communication with the lumen;
   an inflatable member disposed on the tubular member adjacent the distal end and in communication with the lumen;
   a sheath slidably disposed on the tubular member to selectably enclose the inflatable member during retrieval;
   a catheter having proximal and distal ends, a lumen extending therethrough, and a blood outlet port in communication with the lumen, the catheter adapted to be disposed in a patient's carotid artery, the elongated tubular member and inflatable member configured to pass through the lumen;
   an occlusion element disposed on the distal end of the catheter and having an opening that communicates with the lumen, the occlusion element having a contracted state suitable for transluminal insertion and an expanded state wherein the occlusion element occludes antegrade flow in the artery;
   a venous return catheter having proximal and distal ends, a lumen extending therethrough, and a blood inlet port in communication with the lumen; and
   tubing that couples the blood outlet port to the blood inlet port.

10. The apparatus of claim 9 wherein the elongated tubular member comprises discrete proximal and distal sections connected at a junction.

11. The apparatus of claim 10 further comprising a tube fixedly disposed within the lumen to support the junction.

12. The apparatus of claim 10 wherein at least a portion of the distal section is radiopaque.

13. The apparatus of claim 12 further comprising a coil fixedly disposed within the inflatable member, the coil extending beyond a distal end of the tubular member.

14. The apparatus of claim 9 wherein the inflatable member has a deployed state and a retrieval state.

15. The apparatus of claim 9 further comprising a blood filter coupled between the blood outlet port and the blood inlet port.

16. The apparatus of claim 9 wherein the occlusion element is a balloon.

17. The apparatus of claim 9 further comprising a pump that removes blood through the catheter and reperfuses blood via the venous return catheter.

* * * * *